(12) United States Patent
Natarajan et al.

(10) Patent No.: US 10,993,673 B2
(45) Date of Patent: May 4, 2021

(54) TECHNOLOGIES FOR BIOSIGNAL FEEDBACK FILTERING

(71) Applicant: INTEL CORPORATION, Santa Clara, CA (US)

(72) Inventors: Venkat Natarajan, Bangalore (IN); Sowmya Jonnada, Kakinada (IN)

(73) Assignee: Intel Corporation, Santa Clara, CA (US)

( * ) Notice: Subject to any disclaimer, the term of this patent is extended or adjusted under 35 U.S.C. 154(b) by 767 days.

(21) Appl. No.: 15/531,177

(22) PCT Filed: Nov. 25, 2015

(86) PCT No.: PCT/US2015/062681
§ 371 (c)(1),
(2) Date: May 26, 2017

(87) PCT Pub. No.: WO2016/105835
PCT Pub. Date: Jun. 30, 2016

(65) Prior Publication Data
US 2017/0325748 A1    Nov. 16, 2017

(30) Foreign Application Priority Data
Dec. 27, 2014    (IN) .......................... 6625/CHE/2014

(51) Int. Cl.
*A61B 5/00* (2006.01)
*A61B 5/04* (2006.01)
(Continued)

(52) U.S. Cl.
CPC ........ *A61B 5/7264* (2013.01); *A61B 5/04017* (2013.01); *A61B 5/7225* (2013.01); *A61B 5/7271* (2013.01); *A61B 5/7278* (2013.01); *A61B 5/7282* (2013.01); *A61B 5/01* (2013.01); *A61B 5/0402* (2013.01);
(Continued)

(58) Field of Classification Search
CPC ... A61B 5/7264; A61B 5/7271; A61B 5/7278; A61B 5/7282; G16H 50/20; G16H 50/30
See application file for complete search history.

(56) References Cited

U.S. PATENT DOCUMENTS 9,314,167 B2 *   4/2016   LeBoeuf .............. A61B 5/6817
2003/0187341 A1 * 10/2003   Sackner .............. A61B 5/0245
                                                           600/388
(Continued)

OTHER PUBLICATIONS

International search report for PCT application No. PCT/US2015/062681, dated Mar. 15, 2016 (4 pages).
(Continued)

*Primary Examiner* — John R Downey
(74) *Attorney, Agent, or Firm* — Alliance IP, LLC (57) ABSTRACT

Technologies for filtering biosignals include one or more biosignal sensors coupled to a user to receive biosignals and a computing device to receive biosignals from the biosignal sensors. The biosignal sensors filter the received biosignals to identify abnormal biosignals using a plurality of domain filters including a time domain filter and a frequency domain filter. The biosignals identified as abnormal by each of the domain filters are transmitted to the computing device, while the remaining biosignals are discarded.

25 Claims, 7 Drawing Sheets

(51) Int. Cl.
*A61B 5/01* (2006.01)
*A61B 5/053* (2006.01)
*A61B 5/0402* (2006.01)
*A61B 5/0476* (2006.01)
*A61B 5/0488* (2006.01)
*A61B 5/0533* (2021.01)
*A61B 5/0537* (2021.01)
*A61B 5/0531* (2021.01)

(52) U.S. Cl.
CPC .......... *A61B 5/0476* (2013.01); *A61B 5/0488* (2013.01); *A61B 5/0531* (2013.01); *A61B 5/0533* (2013.01); *A61B 5/0537* (2013.01)

(56) References Cited

U.S. PATENT DOCUMENTS

| | | | |
|---|---|---|---|
| 2006/0094943 A1* | 5/2006 | Van Slyke | A61B 5/14551 600/323 |
| 2010/0249611 A1* | 9/2010 | Chen | A61B 5/0816 600/484 |
| 2010/0286533 A1 | 11/2010 | Lee et al. | |
| 2011/0054359 A1 | 3/2011 | Sazonov et al. | |
| 2011/0319724 A1* | 12/2011 | Cox | A61B 5/02028 600/301 |
| 2012/0108983 A1 | 5/2012 | Banet et al. | |
| 2013/0060100 A1* | 3/2013 | Wurm | A61B 7/003 600/301 |
| 2013/0197380 A1* | 8/2013 | Oral | A61B 5/0452 600/518 |
| 2013/0237872 A1* | 9/2013 | Zhang | A61B 5/686 600/513 |
| 2015/0223701 A1* | 8/2015 | Ghaemi | A61B 5/0205 600/430 |
| 2016/0296156 A1* | 10/2016 | Conradsen | G16H 40/63 |

OTHER PUBLICATIONS

Written opinion for PCT application No. PCT/US2015/062681, dated Mar. 15, 2016 (8 pages).
Indian Office action for Indian patent application No. 6625/CHE/2014, dated Feb. 12, 2020 (9 pages).
Addision, Paul S., "Wavelet transforms and the ECG: a review," Institute of Physics Publishing, Physiol. Meas. 26 (2005) R155-R199 (45 pages).
Afsar Minhas, Fayyaz-ul-Amir, "Robust electrocardiogram (ECG) beat classification using discrete wavelet transform," IOP Publishing, Physiol. Meas. 29 (2008) 555-570 (16 pages).
Jayachandran, E.S. et al., "Analysis of Myocardial Infarction Using Discrete Wavelet Transform," J Med Syst (2010) 34:985-992 (8 pages).
Karpagachelvi, S. et al., "ECG Feature Extraction Techniques—A Survey Approach," (IJCSIS) International Journal of Computer Science and Information Security, vol. 8, No. 1, Apr. 2010 (5 pages).
Tan, K.F. et al., "Detection of the QRS Complex, P Wave and T Wave in Electrocardiogram," Department of Electronic Engineering, City University of Hong Kong, Hong Kong, 2000 First International Conference Advances in Medical Signal and Information Processing (IEE Conf. Publ. No. 476), Bristol, UK, 2000, pp. 41-47, doi: 10.1049/cp:20000315 (7 pages).
Valens, C., "A Really Friendly Guide to Wavelets," (1999), (19 pages).

* cited by examiner

TECHNOLOGIES FOR BIOSIGNAL FEEDBACK FILTERING

CROSS REFERENCE TO RELATED APPLICATIONS

The present application is a national stage entry under 35 USC § 371(b) of International Application No. PCT/US2015/062681, which was filed Nov. 25, 2015, claims priority to Indian Patent Application Serial No. 6625/CHE/2014, entitled "TECHNOLOGIES FOR BIOSIGNAL FEEDBACK FILTERING," which was filed on Dec. 27, 2014.

BACKGROUND

Typical continuous biofeedback monitoring systems include biosignal sensors in contact with a user to capture and measure biosignals of the user, which are generally transmitted from the biosignal sensors to a centralized wearable, mobile, or stationary computing device for display and interpretation. The biosignal sensors, forming a wireless network commonly referred to as a body area network (BAN), may be used to sense electrical activity of organs, including heart rate, brain activity, temperature, and muscular action. For example, brain activity may be monitored in electroencephalogram (EEG) systems, heart activity may be monitored in electrocardiogram (ECG) systems, and skeletal muscle activity may be monitored in electromyogram (EMG) systems. Certain biofeedback monitoring systems may additionally or alternatively use biosignal sensors to sense electrical resistance (e.g., a galvanic skin response), skin moisture or temperature, or magnetic fields (e.g., a Magnetoencephalogram, or MEG), while still other biosignal sensors may be used for neurovascular coupling (e.g., a functional near-infrared spectroscopy, or fNIR) to sense blood flow.

One of the challenging aspects of using traditional biosignal sensors in a BAN involves power drain attributable to continuous ambulatory monitoring by the biosignal sensors. Continuous ambulatory monitoring involves continuously sensing and transmitting monitored biosignals to the centralized computing device in order to provide real-time feedback to ensure a proper diagnosis of the sensed biosignals and, consequently, the health of the user. Additionally, continuous ambulatory sensing involves the generation of a large amount of signal data that must be streamed from the biosignal sensors to the centralized computing device, which typically has a significant negative impact on battery life and is network-intensive. Additionally, depending on the type of biosignals being monitored by the biofeedback monitoring system, the biosignal sensors may be implanted into the skin of the body, directly attached to the skin of the body, or in proximity to the skin of the body, such as in a wearable sensor (e.g., a wrist worn pulse monitoring sensor). As such, the biosignal sensors are typically housed in a small form factor, which reduces the available space for hardware necessary to accommodate large power supplies, extra memory, etc. In other words, simply adding hardware to resolve the power drain and excessive network bandwidth usage is not always a viable option.

Presently, various methods have been used to reduce the power consumption of the sensors, including intermittent biosignal monitoring, localized data batching, and the use of low-power integrated circuits (ICs) in the biosignal sensors. However, intermittent monitoring may result in pertinent biosignal information being lost due to the fact that not all of the sensed biosignals are transmitted to the centralized computing device for further analysis. Additionally, localized data batching requires additional memory and increased bandwidth, which, as noted previously, is not always an option due to the small form factor and may not meet the real-time requirement, as well. Further, the use of low-power ICs impacts the power consumption associated with the sensing and processing of the signal data, but may not appreciably impact the network bandwidth usage for data transmission, or the power consumption attributable to the transmission of the data.

BRIEF DESCRIPTION OF THE DRAWINGS

The concepts described herein are illustrated by way of example and not by way of limitation in the accompanying figures. For simplicity and clarity of illustration, elements illustrated in the figures are not necessarily drawn to scale. Where considered appropriate, reference labels have been repeated among the figures to indicate corresponding or analogous elements.

DETAILED DESCRIPTION OF THE DRAWINGS

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. Additionally, it should be appreciated that items included in a list in the form of "at least one of A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

The disclosed embodiments may be implemented, in some cases, in hardware, firmware, software, or any combination thereof. The disclosed embodiments may also be implemented as instructions carried by or stored on one or more transitory or non-transitory machine-readable (e.g., computer-readable) storage media, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Figure 1:
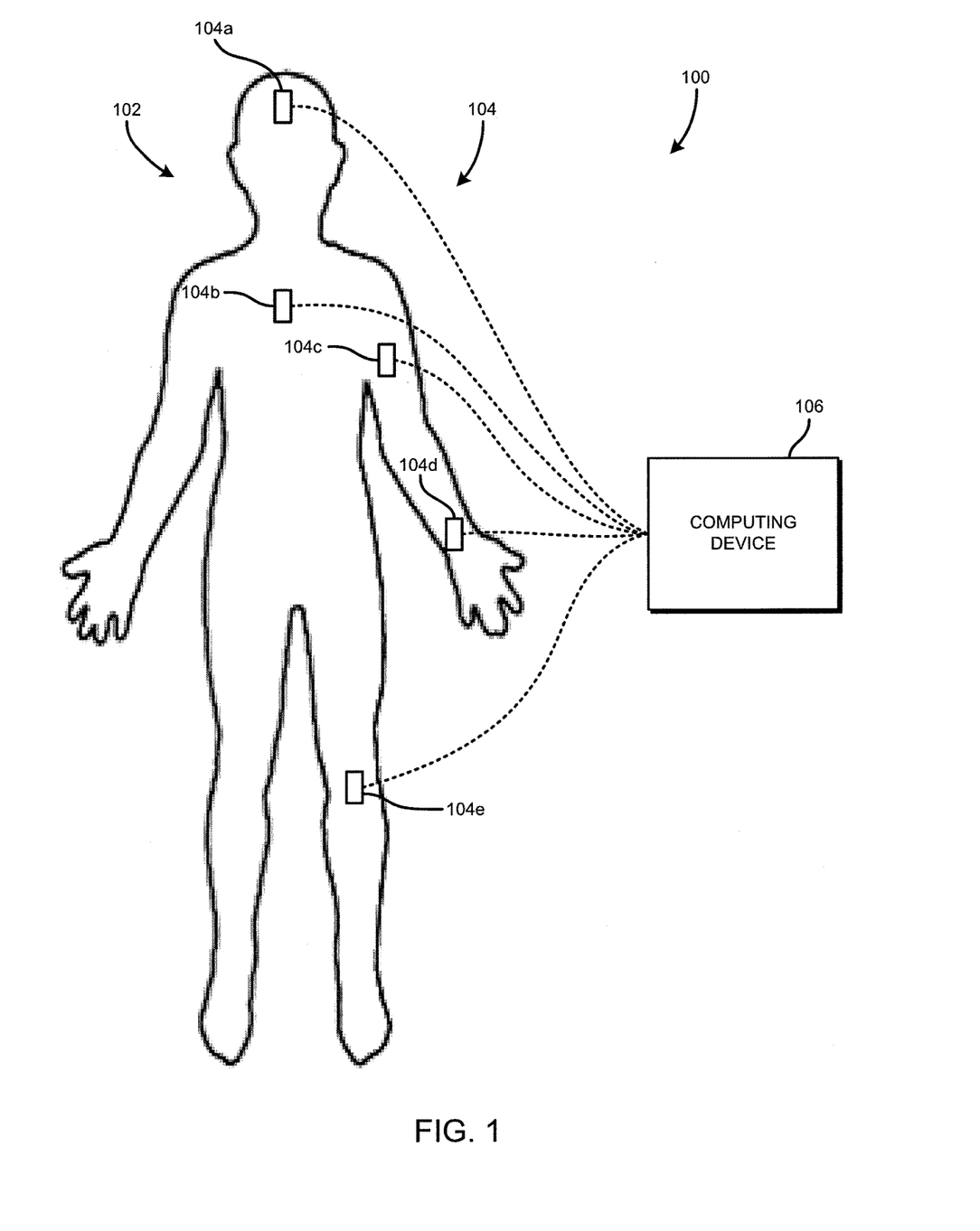
FIG. 1 is an illustration of at least one embodiment of a body area network (BAN) including biosignal sensors in communication with a computing device.

Referring now to FIG. 1, an illustrative biofeedback monitoring system 100 includes one or more biosignal sensors 104 coupled to a body of a user 102 and a computing device 106, generally forming a body area network (BAN). In use, as discussed in more detail below, the biosignal sensors 104 are coupled to the user to continually, continuously, or periodically sense biosignals, or biomedical signals, of the body of the user 102, process and filter the sensed biosignals, and transmit the filtered biosignals to the computing device 106 based on a classification of the filtered biosignals. The biosignals may include any signal of the user 102 that can be continually measured or monitored, such as an electrical activity level of an organ, a galvanic skin response, a skin temperature, a skin moisture level, and/or other biosignal.

It should be appreciated that each transmission of the sensed biosignals from the biosignal sensors 104 to the computing device 106 results in an amount of power drain on the corresponding biosignal sensor 104. Additionally, depending on the number of biosignal sensors 104 in use in the system 100, and the type and amount of data being transmitted, the network bandwidth usage may exceed the available network bandwidth, result in a higher number of collisions across the network, and/or inhibit other pertinent usage of the network if all biosignal sensors 104 transmit data at the same time. Further, in some embodiments, the biosignal sensors 104 may require a form factor that is restricted in size, typically based on the type of biosignals being sensed by the biosignal sensors 104. In one example, the biosignal sensors 104 may be implanted in the user, therefore requiring a small form factor to accommodate the user 102. In another example, to allow the user 102 to be able to move without restraint caused by wearable biosignal sensors 104, the biosignal sensors 104 may necessarily be restricted in size. The size restriction in such embodiments may inhibit the possibility of incorporating additional and/or larger power sources to increase the lifespan of the biosignal sensors 104, as well as additional hardware to increase the compute ability and storage availability.

Accordingly, as discussed in more detail below, the biosignal sensors 104 of the system 100 are configured to limit or reduce the overall number of biosignal transmissions. To do so, the biosignal sensors 104 transmit only those biosignals corresponding to changes of the biosignals, such as relative to a baseline (i.e., a threshold). In use, as will be described in further detail below, the biosignal sensors 104 apply a multi-stage, or multi-level, series of orthonormal domain filters to the biosignals to classify the biosignals as normal (i.e., not sufficiently deviated from the baseline) or abnormal (i.e., sufficiently deviated from the baseline), and only transmit those biosignals classified as abnormal across each stage of the multi-stage series of orthonormal domain filters. Unlike traditional continuous transmission techniques, transmitting only those biosignals classified as abnormal across each stage of the multi-stage series of orthonormal domain filters results in fewer transmissions, and therefore, less network bandwidth and power being used by the biosignal sensors 104. Using less bandwidth may result in less congestion on the biofeedback monitoring system 100, and likely an increase in rate of success of successful data transmission (i.e., fewer collisions). Further, applying the multi-stage series of filters reduces unnecessary transmissions attributed to false negatives, as well as false positives, thereby further decreasing bandwidth usage and increasing the confidence of the user 102, or operator, of the accuracy of the selected biosignal transmissions.

In the illustrative biofeedback monitoring system 100 of FIG. 1, the biosignal sensors 104 include an EEG sensor 104a, an ECG sensor 104b, a blood pressure sensor 104c, a pulse sensor 104d, and an EMG sensor 104e. Of course, it should be appreciated that the biofeedback monitoring system 100 is intended for illustrative purposes only, and may include fewer, additional, or alternative sensors than those shown in FIG. 1. In use, each biosignal sensor 104 is configured to sense biosignals of the body of the user 102. The biosignal sensors 104 may detect, based on the type of sensor, various biosignals including electrical activity of organs, skin temperature, skin moisture, etc. For example, the EEG sensor 104a may be used to sense electrical activity of the brain of the user 102, the ECG sensor 104b may be used to sense electrical activity of the heart of the user 102, and the EMG sensor 104e may be used to sense electrical activity of the skeletal muscle of the user 102. It should be appreciated that biofeedback monitoring systems may include one or more of a single type of biosignal sensor 104, or multiple types of biosignal sensors 104 such as the illustrative biofeedback monitoring system 100. The sensed biosignals are typically transmitted to the computing device 106 for further analysis and display. For example, sensed biosignals transmitted to the computing device 106 from the ECG sensor 104b may be analyzed at the computing device 106 to determine heart rate variability, which may, in turn, be used to determine an emotional state of the user 102.

The computing device 106 of the illustrative biofeedback monitoring system 100 is configured to receive the transmitted biosignals from the biosignal sensors 104 and generate biofeedback data based on the received biosignals. The computing device 106 may be embodied as any type of device capable of performing the functions described herein. For example, the computing device 106 may be embodied as, without limitation, a computer, a desktop computer, a workstation, a server computer, a laptop computer, a notebook computer, a tablet computer, a smartphone, a mobile computing device, a wearable computing device, a distributed computing system, a multiprocessor system, a consumer electronic device, a smart appliance, and/or any other computing device capable of receiving the transmitted biosignals from the biosignal sensors 104 and generating biofeedback data based on the received biosignals. In some embodiments, the computing device 106 may be a remote computing device that is connected to the biosignal sensors 104 via a network device (not shown), such as an access point, for example. In other embodiments, the computing device 106 may be embodied as a wearable computing device (e.g., a smartwatch or smart clothing) worn by the user 102. Additionally, in some embodiments, the computing device 106 may also include one or more peripheral devices (not shown). The peripheral devices may include any number of additional input/output devices, interface devices, and/or other peripheral devices. For example, in some embodiments, the peripheral devices may include a display, touch screen, graphics circuitry, keyboard, mouse, speaker system, and/or other input/output devices, interface devices, and/or other peripheral devices.

Figure 2:
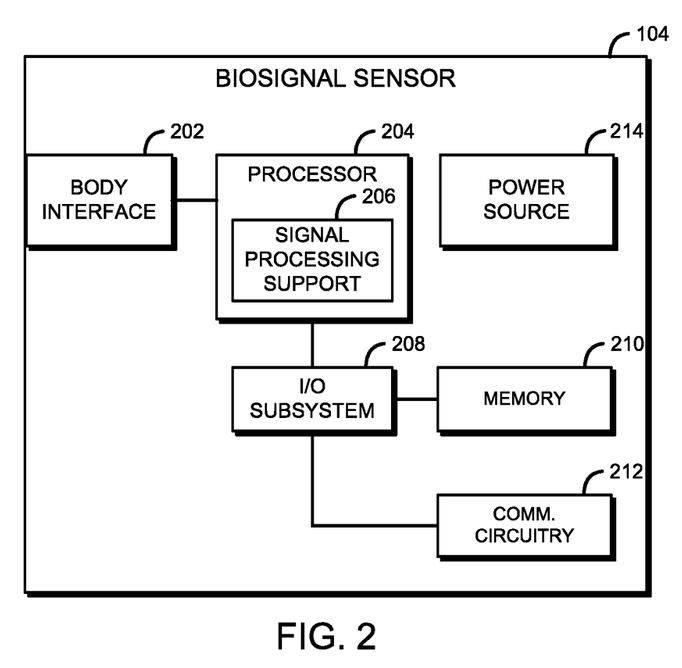
FIG. 2 is a simplified block diagram of at least one embodiment of a biosignal sensor of the BAN of FIG. 1.

Referring now to FIG. 2, each illustrative biosignal sensor 104 includes a body interface 202, a processor 204, an input/output (I/O) subsystem 208, a memory 210, communication circuitry 212, and a power source 214. Of course, it should be appreciated that the biosignal sensor 104 may include additional and/or alternative components not shown in FIG. 2, including those components found in a typical biosignal sensor. The body interface 202 may be embodied as any type of interface capable of facilitating the transmission or reception of a biosignal at the biosignal sensor 104 via the body of the user 102. The body interface 202 may be in direct and/or indirect contact with the body of the user 102 to detect the biosignals, depending on the type of biosignals being monitored, or measured, by the biosignal sensor 104. For example, the body interface 202 may be embodied as a conductive plate (e.g., metallic plate), a probe, wires, or other connection capable of communicatively coupling the biosignal sensor 104 to the body of the user 102. In some embodiments, the body interface 202 may be in contact with the skin of the user 102 via a conductive medium (i.e., a wet contact interface), such as an electrically conductive gel. In other embodiments, the body interface 202 may be in direct contact with the skin of the user 102 (i.e., a dry contact interface). In dry contact interface embodiments, the body interface 202 may only require the biosignal sensors 104 be in near proximity to the skin of the user 102 (i.e., a wearable device), such as on the outside of clothing, or inside of a pocket, rather than in direct contact with the skin of the user 102. In such embodiments, the biosignal sensor 104 may include a strap or other devices to secure the wearable device to the body of the user 102. It should be appreciated that, in some embodiments, the body interface 202 may be embodied as multiple contacts (e.g., multiple conductive plates) depending on the type of biosignals being measured and/or other criteria (e.g., in biosignals sensors in which a galvanic skin response is measured). It should be further appreciated that, in some embodiments, each of the biosignal sensors 104 of the biofeedback monitoring system 100 may include different contact interface types (i.e., wet and/or dry contact interfaces).

The processor 204 may be embodied as any type of processor capable of performing the functions described herein. For example, the processor 204 may be embodied as a single or multi-core processor(s), digital signal processor, microcontroller, or other processor or processing/controlling circuit. The illustrative processor 204 includes signal processing support 206. The signal processing support 206 may be embodied as any hardware, microcode, firmware, or other components of the processor 204 capable of conditioning and/or other otherwise processing the biosignals received by the body interface 202. As further described below, the signal processing support 206 may include processor instructions or other hardware commands to filter the biosignals. It should be appreciated that the signal processing support 206 may form a specialized sensor circuit including, but not limited to, a body organ electrical activity sensor, a galvanic skin response sensor, a skin moisture sensor, and/or a skin temperature sensor.

The memory 210 may be embodied as any type of volatile or non-volatile memory or data storage capable of performing the functions described herein. In operation, the memory 210 may store various data and software used during operation of the biosignal sensor 104. The memory 210 is communicatively coupled to the processor 204 via the I/O subsystem 208, which may be embodied as circuitry and/or components to facilitate input/output operations with the processor 204, the memory 210, and other components of the biosignal sensor 104. For example, the I/O subsystem 208 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 208 may form a portion of a system-on-a-chip (SoC) and be incorporated, along with the processor 204, the memory 210, and other components of the biosignal sensor 104, on a single integrated circuit chip.

The communication circuitry 212 may be embodied as any communication circuit, device, or collection thereof, capable of enabling communications between the biosignal sensor 104 and the computing device 106. The communication circuitry 212 may be configured to use any one or more communication technologies (e.g., wireless or wired communications) and associated protocols (e.g., Ethernet, Bluetooth®, Wi-Fi®, WiMAX, etc.) to effect such communication.

The power source 214 is configured to supply power to the various components of the biosignal sensor 104. In an illustrative embodiment, the power source 214 is embodied as a battery, though it should be appreciated that the power source 214 may be embodied as any type of power supplying source capable of supplying power to each of the components of the biosignal sensor 104. In some embodiments, the power source 214 may be embodied as a rechargeable power source.

Figure 3:
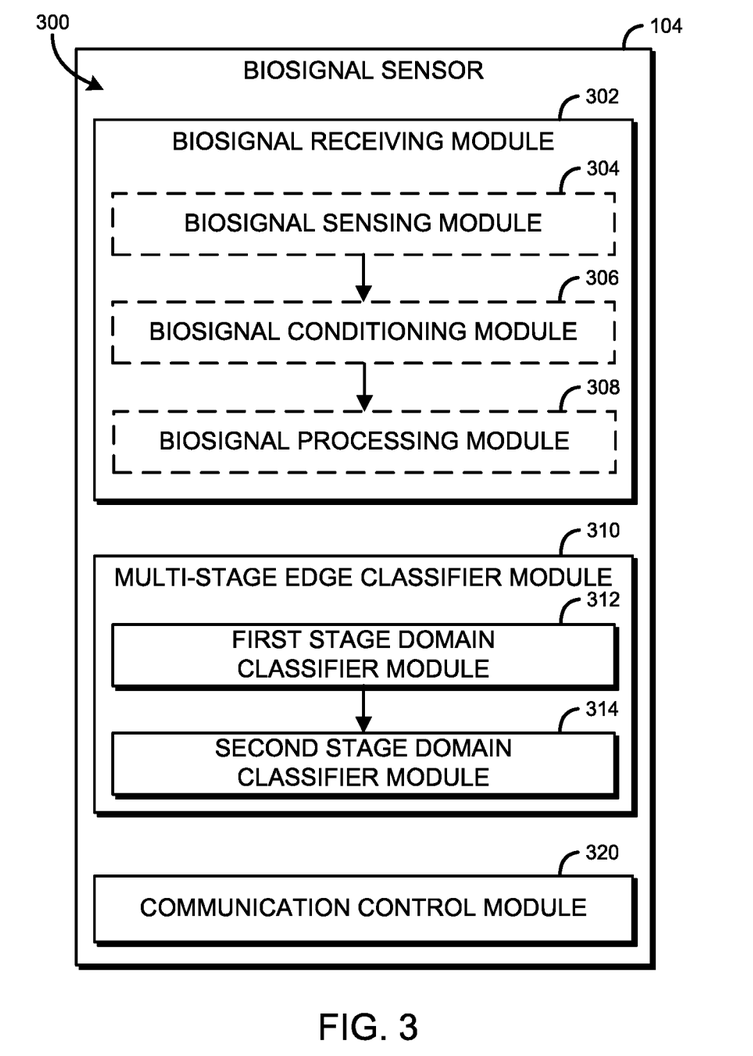
FIG. 3 is a simplified block diagram of at least one embodiment of an environment of the biosignal sensor of FIG. 2.

Referring now to FIG. 3, in use, each of the biosignal sensors 104 establishes an environment 300 during operation. The illustrative environment 300 includes a biosignal receiving module 302, a multi-stage edge classifier module 310, and a communication control module 320. The various modules of the environment 300 may be embodied as hardware, firmware, software, or a combination thereof. For example the various modules, logic, and other components of the environment 300 may form a portion of, or otherwise be established by, the processor 204 or other hardware components of the biosignal sensor 104. As such, in some embodiments, any one or more of the modules of the environment 300 may be embodied as a circuit or collection of electrical devices (e.g., a biosignal receiving circuit, a multi-stage edge classifier circuit, a communication control circuit, etc.).

The biosignal receiving module 302 is configured to receive the biosignals from the body of the user 102. In some embodiments, during execution, the biosignal receiving module may receive the biosignals every duty cycle of the processor 204 and filter the biosignals to isolate a particular subset of the received biosignals corresponding to the type of biosignals being sensed by the biosignal sensor 104 that received the biosignals. For example, a biosignal sensor 104 configured to sense biosignals corresponding to activity of the heart of the user, such as the ECG sensor 104b of FIG. 1, may filter out biosignals received from the BAN that are outside of the normal frequency range of an ECG biosignal (e.g., 0-100 Hz). Additionally, the biosignal receiving module may be further configured to condition the biosignal (e.g., filter, amplify, de-noise, etc.) and/or process the biosignal (e.g., convert the analog signal to a digital signal). In some embodiments, one or more of those functions may be performed by sub-modules, such as a biosignal sensing module 304, a biosignal conditioning module 306, and/or a biosignal processing module 308. Additionally, it should be appreciated that, in some embodiments, the biosignal receiving module 302 may include more than one of the biosignal sensing module 304, the biosignal conditioning module 306 and/or the biosignal processing module 308 to facilitate the sensing of different types of biosignals.

The multi-stage edge classifier module 310 is configured to classify the received biosignals as normal or abnormal depending on the type of biosignal being monitored. The illustrative multi-stage edge classifier module 310 includes a first stage domain classifier module 312 and a second stage domain classifier module 314. While the illustrative multi-stage edge classifier module 310 has been shown as a two-stage classifier module (i.e., the first and second stage domain classifier modules 312, 314), it should be appreciated that the multi-stage edge classifier module 310 may include additional stages of domain classifier modules. As will be described in further detail below, in an illustrative embodiment, the first stage domain classifier 312 is embodied as a frequency domain classifier filter and the second stage domain classifier 314 is embodied as a time domain classifier filter. Each of the first and second stage domain classifier modules 312, 314 include a filter bank to transform and/or filter the received biosignals before applying a pass-thru threshold to classify the received biosignals as either normal or abnormal.

As noted previously, the first stage domain classifier module 312 may analyze the received biosignals using a frequency domain classifier filter and a frequency domain threshold. In use, as will be described in further detail below, the first stage domain classifier module 312 determines whether the biosignals are normal, or abnormal, and passes only those biosignals determined to be abnormal to the second stage domain classifier 314. The second stage domain classifier 314 performs a time domain classifier filter and a time domain threshold to determine whether the identified abnormal biosignals are normal, or abnormal. The second stage domain classifier 314 outputs the biosignals classified as abnormal, discarding the biosignals determined to be improperly identified (i.e., false negatives) by the first stage domain classifier module 312. In other words, the second stage domain classifier 314 only outputs the biosignals that have been classified as abnormal in both stages of the illustrative multi-stage edge classifier module 310.

The communication control module 320 is configured to establish a communication connection (i.e., wired or wireless) with a target computing device, such as the computing device 106 of FIG. 1, and transmit the biosignals classified as abnormal in both stages of the illustrative multi-stage edge classifier module 310 to the target computing device. The target computing device may then aggregate, further analyze, and/or display the received abnormal biosignals.

Figure 4:
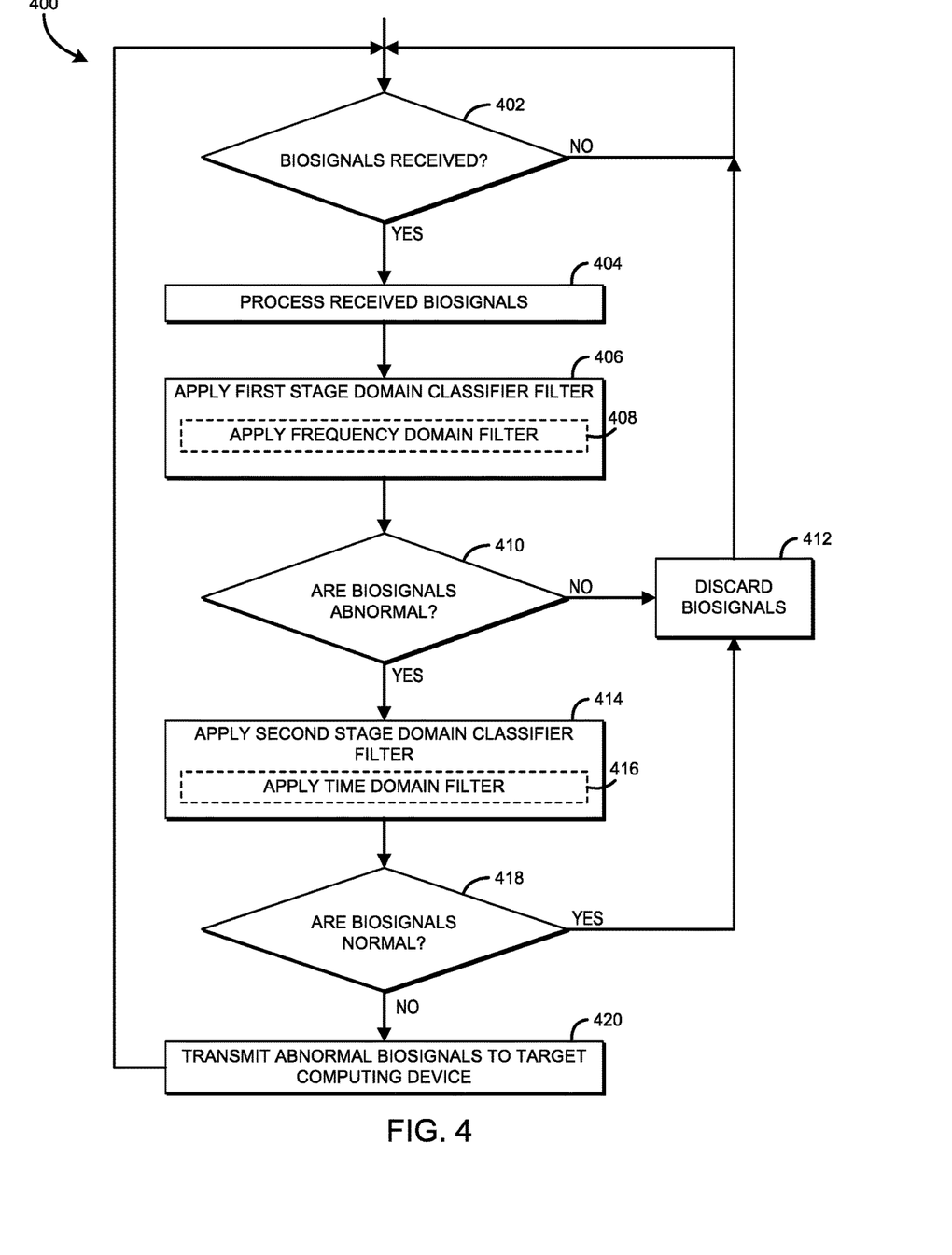
FIG. 4 is a simplified flow diagram of at least one embodiment of a method for filtering biosignals that may be executed by the biosignal sensor of FIGS. 1-3.

Referring now to FIG. 4, in use, each biosignal sensor 104 may execute a method 400 for determining a classification of the biosignals received by the biosignal sensor 104. The method 400 may be executed by hardware of the processor 204, such as by the signal processing support 206. The method 400 begins in block 402, in which the biosignal sensor 104 determines whether biosignals have been received. If not, the method 400 loops back to block 402 to continue monitoring for received biosignals. In block 404, the biosignal sensor 104 processes the received biosignals. As noted previously, there are various types of biosignals that may be received by the biosignal sensor 104 in a BAN of the user 102, including an electrical activity level of an organ, a galvanic skin response, a skin temperature, and/or a skin moisture level, to name a few. As such, the biosignal sensor may apply one or more filters (e.g., low-pass filters, high-pass filters, band-pass filters, etc.) to isolate only those biosignals for which the biosignal sensor 104 is configured to monitor. Additionally, the biosignal sensor 104 may otherwise process or condition the biosignals at block 404 to remove noise from the biosignals, amplify the biosignals, etc.

In block 406, the biosignal sensor 104 applies a first stage domain classifier filter to classify the biosignals as either normal or abnormal. The first stage domain classifier filter may apply any suitable filter to identify the biosignals as normal or abnormal. For example, in some embodiments, a frequency domain filter may be applied to filter out the normal biosignals in block 408. In use, the frequency domain filter detects abnormal biosignals by filtering the biosignals, such as by a frequency domain basis filter bank (i.e., an array of filters), and compares the resulting filtered biosignals against a threshold (i.e., a baseline). As will be described in further detail below, in some embodiments, the frequency domain filter may classify the biosignals according to a spectral energy threshold in the frequency domain.

In block 410, the biosignal sensor 104 determines whether the biosignals were classified as abnormal by the first stage domain classifier filter in block 406. If the biosignals were not classified as abnormal (i.e., the biosignals are determined to be normal), the method 400 advances to block 412, where the biosignals are discarded before the method 400 loops back to block 402. If the biosignals were classified as abnormal, the method 400 advances to block 414 in which the biosignal sensor 104 applies a second stage domain classifier filter to classify the biosignals as either normal or abnormal. It should be appreciated that, while the first stage domain classifier filter may identify abnormal biosignals, some of the identified "abnormal" biosignals may actually be normal (i.e., the first stage domain classifier filter may generate false positives). To improve the accuracy of the classification process, the second stage domain classifier filter further filters the biosignals identified as "abnormal" by the first stage domain classifier to affirm the identified "abnormal" biosignals as abnormal, or reject the identified "abnormal" biosignals as normal.

The second stage domain classifier filter may apply any type of suitable filter to identify the biosignals as normal or abnormal. For example, in some embodiments, in block 416, a time domain filter may be applied to filter out the normal biosignals. In use, the time domain filter detects normal biosignals by further filtering the abnormal biosignals, such as by a time domain basis filter bank (i.e., an array of filters), and compares the resulting further filtered biosignals against a threshold (i.e., a baseline). As will be described in further detail below, in some embodiments, the threshold may be determined based on a hysteresis of past classifications.

It should be appreciated that because a two-stage (or multi-stage) classification process is used in the illustrative embodiment, the first stage domain classifier filter may be selected based on its ability to identify abnormal biosignals (e.g., a frequency domain filter), even though such filter may have an increased rate of false positives (i.e., identifying normal biosignals as abnormal). Similarly, the second stage domain classifier filter may be selected based on its ability to identify normal biosignals (e.g., a time domain filter), even though such filter may have an increased rate of false negatives (i.e., identifying a normal biosignal as abnormal).

In block 418, the biosignal sensor 104 determines whether the biosignals were classified as normal by the second stage domain classifier filter in block 414. If the biosignals were classified as normal, the method 400 advances to block 412, wherein the biosignals are discarded before the method 400 loops back to block 402 to continue monitoring for new biosignals. If the biosignals were not classified as normal, the method 400 advances to block 420. In block 420, the biosignal sensor 104 transmits the abnormal biosignals to a target computing device, such as the computing device 106 of FIG. 1, for further aggregation, analysis, and/or display to the user 102, or operator, of the biofeedback monitoring system 100. It should be appreciated that, by only transmitting the abnormal biosignals, the bandwidth and number of transmissions are decreased relative to a continuously transmitting biosignal sensor. As such, the power consumption attributed to the transmissions from the biological sensor 104 is also decreased over a period of time as compared to that of the continuously transmitting biosignal sensor. In other words, the operable lifespan of the biosignal sensor 104 selectively transmitting abnormal biosignals is increased compared to that of the continuously transmitting biosignal sensor having the same initial power level/capacity.

Figure 5:
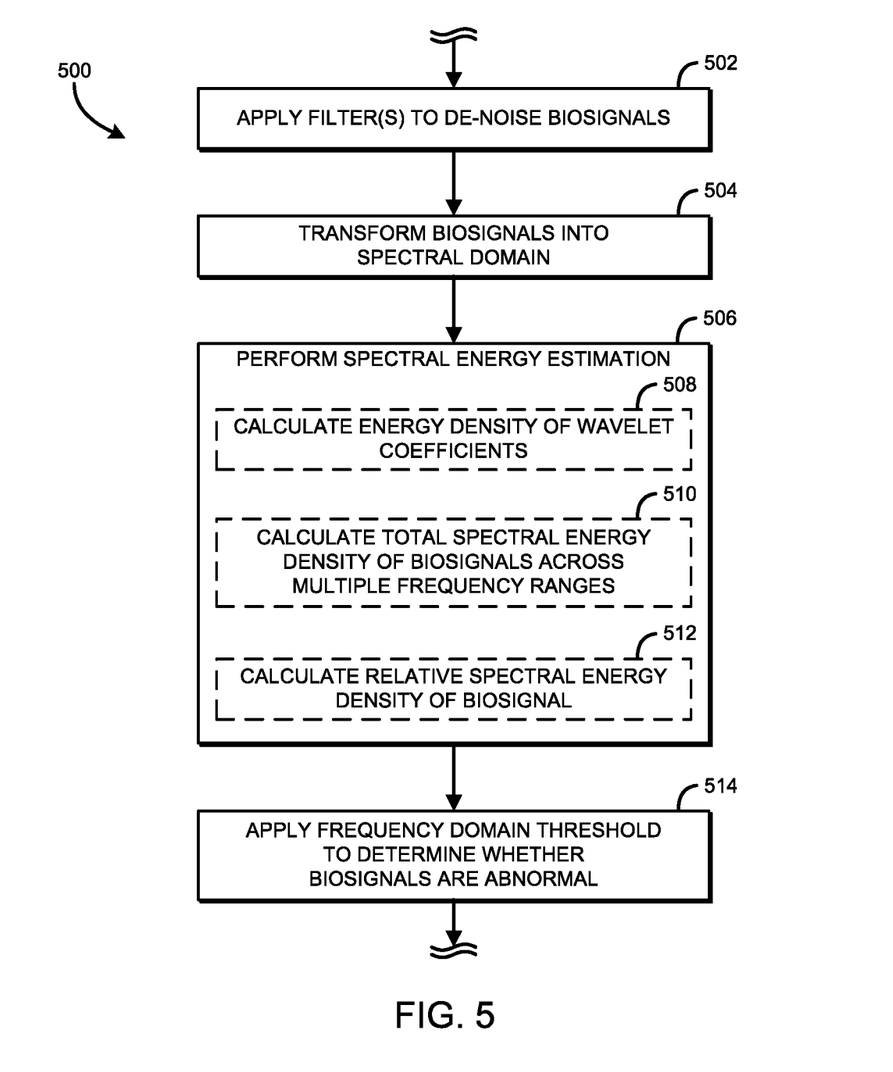
FIG. 5 is a simplified flow diagram of at least one embodiment of a method for applying a frequency domain filter to the biosignals that may be executed by the biosignal sensor of FIGS. 1-3.

Referring now to FIG. 5, as discussed above, the biosignal sensor 104 applies a first stage domain classifier filter in block 406 of method 400. To do so, the biosignal sensor 104 may execute a method 500 for applying a frequency domain filter to classify the biosignals as either normal or abnormal. The method 500 begins in block 502, in which the biosignal sensor 104 applies one or more filters to de-noise the biosignals. In block 504, the biosignals are transformed into the spectral domain using a filter bank that includes multiple levels of decomposition based on a sampling frequency of the biosignal. In some embodiments, the biosignal may be transformed into the spectral domain using a discrete wavelet transform (DWT) dyadic algorithm, such as Daubechies wavelet db6, for example. At each level of the filter bank (i.e., DWT scale), the dyadic DWT may compute a set of wavelet coefficients that correspond to a scaled-down low-frequency range (i.e., approximate coefficients) and a scaled-up high-frequency range (i.e., detailed coefficients). In some embodiments, the set of wavelet coefficients may be computed across multiple frequency ranges (i.e., levels) corresponding to the biosignals monitored by the biosignal sensor 104, an example of which is described in further detail in FIG. 7. In some embodiments, the biosignal sensor 104 may calculate the energy density of the wavelet coefficients across one or more of the multiple frequency ranges corresponding to the type of biosignal being monitored by the biosignal sensor, as in block 508. In some embodiments, as in block 510, the biosignal sensor 104 may calculate the total spectral energy density of the biosignals across the multiple frequency ranges. In some embodiments, in block 512, the biosignal sensor 104 may calculate the relative spectral density of the biosignals as a function of the energy density of the wavelet coefficients across one or more of the multiple frequency ranges calculated in block 508 and the total spectral energy density of the biosignal across the multiple frequency ranges calculated in block 510.

Figure 7:
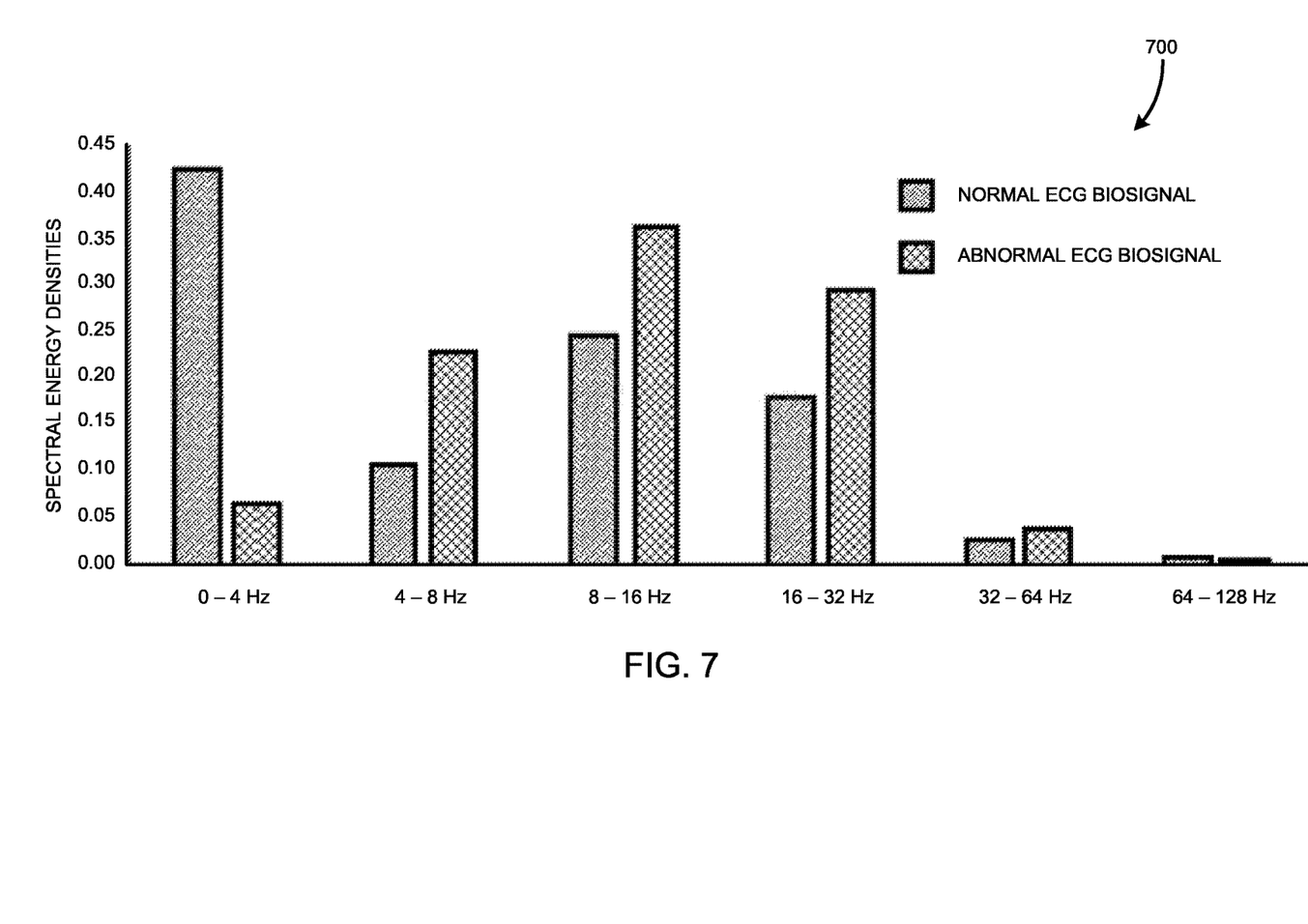
FIG. 7 is a graph illustrating example normalized spectral energy densities of normal and abnormal ECG biosignals.

In an illustrative embodiment of a biosignal sensor 104 in an ECG biosignal sensing system, FIG. 7 illustrates a graph 700 of normalized spectral energy densities for normal and abnormal ECG biosignals in five ranges (i.e., levels) between 0 Hz and 128 Hz. As can be observed in the graph 700, the normalized spectral energy densities between 8-16 Hz and 16-32 Hz of the wavelet decomposition vary between normal and abnormal ECG biosignals. As such, the normalized spectral energy densities between 8-16 Hz and 16-32 Hz may be used as a spectral energy threshold in the frequency domain to distinguish between normal and abnormal ECG biosignals. In other words, the energy bands in the 8-16 Hz and 16-32 Hz are used to determine the classification of the ECG biosignals. For example, using the normalized spectral energy densities between 8-16 Hz and 16-32 Hz, if the relative energy is greater than 0.14, the ECG biosignals should be classified as normal. If the relative energy is less than or equal to 0.14, the biosignals should be classified as abnormal. Of course, it should be appreciated that the normalized spectral energy densities illustrated in the graph 700 and the spectral energy threshold need not be statically defined (i.e., constant), and may be dynamically adjusted based on the number of energy densities analyzed and/or any other data corresponding thereto. It should be further appreciated that the ECG biosignal classification using the spectral energy threshold may be applied to an ECG biosignal sensing system having any number of biosignal sensors 104 for sensing ECG signals, as the waveform morphology is similar between different ECG sensing biosignal sensors 104.

Figure 6:
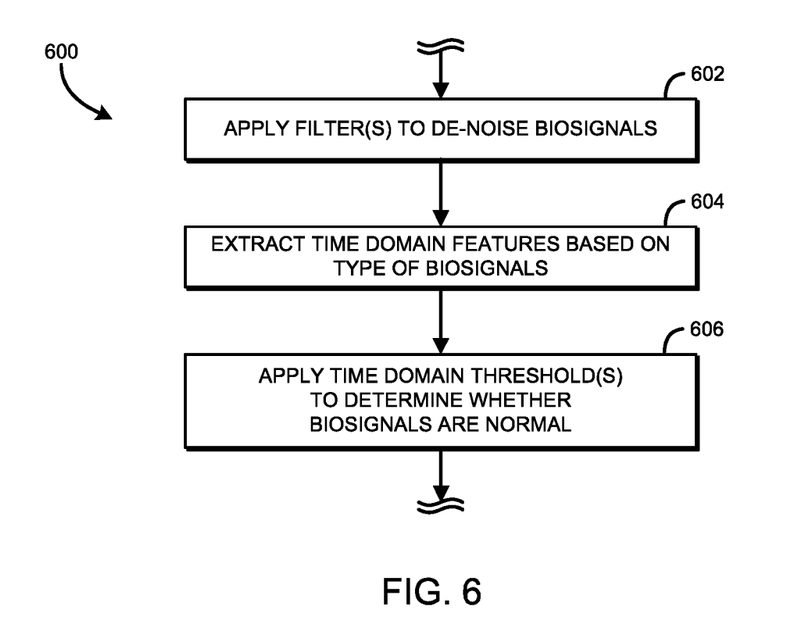
FIG. 6 is a simplified flow diagram of at least one embodiment of a method for applying a time domain filter to the frequency domain filtered biosignals that may be executed by the biosignal sensor of FIGS. 1-3.

Referring now to FIG. 6, as discussed above, the biosignal sensor 104 applies a second stage domain classifier filter in block 414 of method 400. To do so, the biosignal sensor 104 may execute a method 600 for executing a time domain filter to classify the biosignals as either normal or abnormal. The method 600 begins in block 602, in which the biosignal sensor 104 applies one or more filters to de-noise the biosignals. In some embodiments, the biosignals de-noised in block 602 are the raw biosignals corresponding to only those signals classified as abnormal by the frequency domain filter in the method 500. In other words, the biosignals received at the time domain filter in the method 600 for de-noising may be only those biosignals classified as abnormal by the frequency domain filter in the method 500 in their raw form in which they were received at the frequency domain filter in block 502 of the method 500. In block 606, one or more time domain features are determined. In some embodiments, the time domain features may be determined using a derivative method. Fiducial points in the biosignal (e.g., peak locations, peak onsets/offsets, etc.) are identified to calculate time features, such as wave intervals, wave amplitudes, and/or the like.

For example, for an ECG classification, the time domain features (i.e., cardiac signal parameters) may include a heart rate (i.e., a heart rate), a QT interval (i.e., measure of the time between the start of the Q wave and the end of the T wave in the heart's electrical cycle), a PR interval (i.e., P wave to R wave interval), an RR interval (i.e., R wave to R wave interval), a QRS complex (i.e., ventricular depolarization) width, a P wave (i.e., atrial depolarization), and/or a T wave (i.e., repolarization of the ventricles of the heart) amplitude. Each of the time domain features may be used as a threshold to classify the biosignals as either normal or abnormal. For example, in an embodiment using the beat rate as a threshold, a normal ECG biosignal may be determined to be between 60 and 100 beats per second (i.e., a normal resting heart rate). As such, any ECG biosignal having a beat rate of less than 60 beats per second and greater than 100 beats per second would be classified as abnormal. In another example, in an embodiment using the QT interval as a threshold, a normal ECG biosignal may be determined to be less than 0.45 seconds. Therefore, any ECG biosignal with a QT interval greater than 0.45 seconds would be classified as abnormal. In still another example, in an embodiment using the T wave amplitude as a threshold, a positive T wave amplitude may correspond to a normal ECG biosignal, whereas a negative T wave amplitude may correspond to an abnormal ECG biosignal. In yet another example, in an embodiment using the beat rate, the QT interval, and the T wave amplitude as a threshold, a weight may be applied to each of the threshold to allow one threshold to have a stronger influence than another threshold. In such embodiments, the weights may be based on a hysteresis of previous classifications. In block 606, one or more of the time domain features are applied as thresholds to classify the biosignals as either normal or abnormal.

EXAMPLES

Illustrative examples of the technologies disclosed herein are provided below. An embodiment of the technologies may include any one or more, and any combination of, the examples described below.

Example 1 includes a biosignal sensor for the filtering of abnormal biosignals, the biosignal sensor comprising a multi-stage classifier module comprising a plurality of domain filters to filter biosignals of a user of the biosignal sensor so as to identify abnormal biosignals; and a communication control module to transmit the abnormal biosignals to a computing device that is communicatively coupled to the biosignal sensor.

Example 2 includes the subject matter of Example 1, and further including a biosignal receiving module to receive the biosignals from the user, and condition and process the biosignals based on a type of biosignal sensed by the biosignal sensor.

Example 3 includes the subject matter of any of Examples 1 and 2, and wherein to receive the biosignals from the user comprises to receive at least one of an electrical activity level of an organ of the user, an electrical conductance of the skin of the user, a galvanic response of the skin of the user, a temperature of the skin of the user, or a moisture level of the skin of the user.

Example 4 includes the subject matter of any of Examples 1-3, and further including a body interface to receive the biosignals from the user.

Example 5 includes the subject matter of any of Examples 1-4, and wherein to filter the biosignals comprises to filter the biosignals based on a type of the biosignal sensor.

Example 6 includes the subject matter of any of Examples 1-5, and wherein to filter the biosignals comprises to discard those biosignals not identified as abnormal biosignals.

Example 7 includes the subject matter of any of Examples 1-6, and wherein to filter the biosignals comprises to filter the biosignals via a first stage domain classifier filter and a second stage domain classifier filter.

Example 8 includes the subject matter of any of Examples 1-7, and wherein the second stage domain classifier filter is a domain classifier filter in an orthonormal domain of the first stage domain classifier filter.

Example 9 includes the subject matter of any of Examples 1-8, and wherein to filter the biosignals via the second stage domain classifier filter comprises to determine one or more time domain features of the biosignals; to determine a threshold that corresponds to each of the one or more time domain features of the biosignals; and to determine whether the biosignals are normal based on the one or more thresholds that correspond to each of the one or more time domain features of the biosignals.

Example 10 includes the subject matter of any of Examples 1-9, and wherein to filter the biosignals via the first stage domain classifier filter comprises to filter the biosignals via a frequency domain filter.

Example 11 includes the subject matter of any of Examples 1-10, and wherein to filter the biosignals via the second stage domain classifier filter comprises to filter the biosignals via a time domain filter.

Example 12 includes the subject matter of any of Examples 1-11, and wherein to filter the biosignals via the plurality of domain filters to identify abnormal biosignals comprises to transform the biosignals into a spectral domain via a filter bank that includes a plurality of levels, wherein each of the plurality of levels corresponds to a sub-frequency range in a frequency range that corresponds to a type of biosignals received by the biosignal sensor.

Example 13 includes the subject matter of any of Examples 1-12, and wherein to filter the biosignals via the plurality of domain filters to identify abnormal biosignals further comprises to perform a spectral energy estimation of the biosignals transformed in the spectral domain.

Example 14 includes the subject matter of any of Examples 1-13, and wherein to filter the biosignals via the plurality of domain filters to identify abnormal biosignals further comprises to determine whether the biosignals are abnormal based on the spectral energy estimation and a frequency domain threshold.

Example 15 includes the subject matter of any of Examples 1-14, and wherein to perform the spectral energy estimation of the biosignals transformed in the spectral domain comprises to calculate an energy density of wavelet coefficients at each of the plurality of levels.

Example 16 includes the subject matter of any of Examples 1-15, and wherein to perform the spectral energy estimation of the biosignals transformed in the spectral domain further comprises to calculate a total spectral energy density of the biosignals across each of the plurality of levels.

Example 17 includes the subject matter of any of Examples 1-16, and wherein to perform the spectral energy estimation of the biosignals transformed in the spectral domain further comprises to calculate a relative spectral energy density as a function of the energy density of wavelet coefficients at each of the plurality of levels and the total spectral energy density.

Example 18 includes a method for the filtering of abnormal biosignals, the method comprising receiving, by a biosignal sensor coupled to a user, biosignals of the user; filtering, by the biosignal sensor, the biosignals using a plurality of domain filters to identify abnormal biosignals; and transmitting, by the biosignal sensor, the abnormal biosignals to a computing device.

Example 19 includes the subject matter of Example 18, and wherein receiving the biosignals from the user comprises receiving at least one of an electrical activity level of an organ of the user, an electrical conductance of the skin of the user, a galvanic response of the skin of the user, a temperature of the skin of the user, or a moisture level of the skin of the user.

Example 20 includes the subject matter of any of Examples 18 and 19, and wherein receiving the biosignals from a user comprises receiving, with a body interface of the biosensor, biosignals of the user.

Example 21 includes the subject matter of any of Examples 18-20, and wherein filtering the biosignals comprises filtering the biosignals based on a type of biosignal sensed by the biosignal sensor.

Example 22 includes the subject matter of any of Examples 18-21, and wherein filtering the biosignals comprises discarding those biosignals not identified as abnormal bio signals.

Example 23 includes the subject matter of any of Examples 18-22, and wherein filtering the biosignals using the plurality of domain filters to identify abnormal biosignals comprises filtering the biosignals using a first stage domain classifier filter and a second stage domain classifier filter.

Example 24 includes the subject matter of any of Examples 18-23, and wherein filtering the biosignals using the second stage domain classifier filter comprises filtering the biosignals using a domain classifier filter in an orthonormal domain of the first stage domain classifier filter.

Example 25 includes the subject matter of any of Examples 18-24, and wherein filtering the biosignals using the second stage domain classifier filter comprises determining one or more time domain features of the biosignals; determining a threshold corresponding to each of the one or more time domain features of the biosignals; and determining whether the biosignals are normal based on the one or more thresholds corresponding to each of the one or more time domain features of the biosignals.

Example 26 includes the subject matter of any of Examples 18-25, and wherein filtering the biosignals using the first stage domain classifier filter comprises filtering the biosignals using a frequency domain filter.

Example 27 includes the subject matter of any of Examples 18-26, and wherein filtering the biosignals using the second stage domain classifier filter comprises filtering the biosignals using a time domain filter.

Example 28 includes the subject matter of any of Examples 18-27, and wherein filtering the biosignals using the plurality of domain filters to identify abnormal biosignals comprises transforming the biosignals into a spectral domain via a filter bank that includes a plurality of levels, each of the plurality of levels corresponding to a sub-frequency range in a frequency range that corresponds to a type of biosignals being received by the biosignal sensor.

Example 29 includes the subject matter of any of Examples 18-28, and wherein filtering the biosignals using the plurality of domain filters to identify abnormal biosignals further comprises performing a spectral energy estimation of the biosignals transformed in the spectral domain.

Example 30 includes the subject matter of any of Examples 18-29, and wherein filtering the biosignals using the plurality of domain filters to identify abnormal biosignals further comprises determining whether the biosignals are abnormal based on the spectral energy estimation and a frequency domain threshold.

Example 31 includes the subject matter of any of Examples 18-30, and wherein performing the spectral energy estimation of the biosignals transformed in the spectral domain comprises calculating an energy density of wavelet coefficients at each of the plurality of levels.

Example 32 includes the subject matter of any of Examples 18-31, and wherein performing the spectral energy estimation of the biosignals transformed in the spectral domain further comprises calculating a total spectral energy density of the biosignals across each of the plurality of levels.

Example 33 includes the subject matter of any of Examples 18-32, and wherein performing the spectral energy estimation of the biosignals transformed in the spectral domain further comprises calculating a relative spectral energy density as a function of the energy density of wavelet coefficients at each of the plurality of levels and the total spectral energy density.

Example 34 includes a biosignal sensor comprising a processor; and a memory having stored therein a plurality of instructions that when executed by the processor cause the biosignal sensor to perform the method of any of Examples 18-33.

Example 35 includes one or more machine readable storage media comprising a plurality of instructions stored thereon that in response to being executed result in a biosignal sensor performing the method of any of Examples 18-33.

Example 36 includes a biosignal sensor for the filtering of abnormal biosignals, the biosignal sensor comprising means for receiving, by a biosignal sensor coupled to a user, biosignals of the user; means for filtering, by the biosignal sensor, the biosignals using a plurality of domain filters to identify abnormal biosignals; and means for transmitting, by the biosignal sensor, the abnormal biosignals to a computing device.

Example 37 includes the subject matter of Example 36, and wherein the means for receiving the biosignals from the user comprises means for receiving at least one of an electrical activity level of an organ of the user, an electrical conductance of the skin of the user, a galvanic response of the skin of the user, a temperature of the skin of the user, or a moisture level of the skin of the user.

Example 38 includes the subject matter of any of Examples 36 and 37, and wherein the means for receiving the biosignals from a user comprises means for receiving, with a body interface of the biosensor, biosignals of the user.

Example 39 includes the subject matter of any of Examples 36-38, and wherein the means for filtering the biosignals comprises means for filtering the biosignals based on a type of biosignal sensed by the biosignal sensor.

Example 40 includes the subject matter of any of Examples 36-39, and wherein the means for filtering the biosignals comprises means for discarding those biosignals not identified as abnormal biosignals.

Example 41 includes the subject matter of any of Examples 36-40, and wherein the means for filtering the biosignals using the plurality of domain filters to identify abnormal biosignals comprises means for filtering the biosignals using a first stage domain classifier filter and a second stage domain classifier.

Example 42 includes the subject matter of any of Examples 36-41, and wherein the means for filtering the biosignals using the second stage domain classifier comprises means for filtering the biosignals using a domain classifier filter in an orthonormal domain of the first stage domain classifier filter.

Example 43 includes the subject matter of any of Examples 36-42, and wherein the means for filtering the biosignals using the second stage domain classifier comprises means for determining one or more time domain features of the biosignals; means for determining a threshold corresponding to each of the one or more time domain features of the biosignals; and means for determining whether the biosignals are normal based on the one or more thresholds corresponding to each of the one or more time domain features of the biosignals.

Example 44 includes the subject matter of any of Examples 36-43, and wherein the means for filtering the biosignals using the first stage domain classifier filter comprises means for filtering the biosignals using a frequency domain filter.

Example 45 includes the subject matter of any of Examples 36-44, and wherein the means for filtering the biosignals using the second stage domain classifier filter comprises means for filtering the biosignals using a time domain filter.

Example 46 includes the subject matter of any of Examples 36-45, and wherein the means for filtering the biosignals using the plurality of domain filters to identify abnormal biosignals comprises means for transforming the biosignals into a spectral domain via a filter bank that includes a plurality of levels, each of the plurality of levels corresponding to a sub-frequency range in a frequency range that corresponds to a type of biosignals being received by the biosignal sensor.

Example 47 includes the subject matter of any of Examples 36-46, and wherein the means for filtering the biosignals using the plurality of domain filters to identify abnormal biosignals further comprises means for performing a spectral energy estimation of the biosignals transformed in the spectral domain.

Example 48 includes the subject matter of any of Examples 36-47, and wherein the means for filtering the biosignals using the plurality of domain filters to identify abnormal biosignals further comprises means for determining whether the biosignals are abnormal based on the spectral energy estimation and a frequency domain threshold.

Example 49 includes the subject matter of any of Examples 36-48, and wherein the means for performing the spectral energy estimation of the biosignals transformed in the spectral domain comprises means for calculating an energy density of wavelet coefficients at each of the plurality of levels.

Example 50 includes the subject matter of any of Examples 36-49, and wherein the means for performing the spectral energy estimation of the biosignals transformed in the spectral domain further comprises means for calculating a total spectral energy density of the biosignals across each of the plurality of levels.

Example 51 includes the subject matter of any of Examples 36-50, and wherein the means for performing the spectral energy estimation of the biosignals transformed in the spectral domain further comprises means for calculating a relative spectral energy density as a function of the energy density of wavelet coefficients at each of the plurality of levels and the total spectral energy density.

What is claimed is:

1. A wearable biosignal sensor for the filtering of abnormal biosignals, the wearable biosignal sensor comprising:
    a multi-stage classifier module comprising:
        a plurality of domain filters comprising a first domain filter and a second domain filter to filter biosignals of a user of the wearable biosignal sensor so as to identify abnormal biosignals;
        wherein the first domain filter is to:
            receive a first biosignal;
            filter the first biosignal to determine if the first biosignal is abnormal based on the first domain filter;
            in response to a determination that the first biosignal is not abnormal based on the first domain filter, discard the first biosignal; and
            in response to a determination that the first biosignal is abnormal based on the first domain filter, send the first biosignal to the second domain filter,
        wherein the second domain filter is to:
            receive the first biosignal in response to the determination by the first domain filter that the first biosignal is abnormal based on the first domain filter;
            filter the first biosignal to determine if the first biosignal is abnormal based on the second domain filter;
            in response to a determination that the first biosignal is not abnormal based on the second domain filter, discard the first biosignal; and
            in response to a determination that the first biosignal is abnormal based on the second domain filter, send the first biosignal to a communication control module of the wearable biosignal sensor, and
        the communication control module to transmit the first biosignal to a computing device that is communicatively coupled to the wearable biosignal sensor in response to the determination that the first biosignal is abnormal based on the first domain filter and the determination that the first biosignal is abnormal based on the second domain filter.

2. The wearable biosignal sensor of claim 1, wherein the biosignals of the user include at least one of an electrical activity level of an organ of the user, an electrical conductance of the skin of the user, a galvanic response of the skin of the user, a temperature of the skin of the user, or a moisture level of the skin of the user.

3. The wearable biosignal sensor of claim 1, wherein to filter the biosignals comprises to filter the biosignals via a first stage domain classifier filter and a second stage domain classifier filter.

4. The wearable biosignal sensor of claim 3, wherein to filter the biosignals via the first stage domain classifier filter comprises to filter the biosignals via a frequency domain filter.

5. The wearable biosignal sensor of claim 3, wherein to filter the biosignals via the second stage domain classifier filter comprises to filter the biosignals via a time domain filter.

6. The wearable biosignal sensor of claim 3, wherein the second stage domain classifier filter is a domain classifier filter in an orthonormal domain of the first stage domain classifier filter.

7. The wearable biosignal sensor of claim 3, wherein to filter the biosignals via the second stage domain classifier filter comprises:
    to determine one or more time domain features of the biosignals;
    to determine a threshold that corresponds to each of the one or more time domain features of the biosignals; and
    to determine whether the biosignals are normal based on the one or more thresholds that correspond to each of the one or more time domain features of the biosignals.

8. The wearable biosignal sensor of claim 1, wherein to filter the biosignals via the plurality of domain filters to identify abnormal biosignals comprises to transform the biosignals into a spectral domain via a filter bank that includes a plurality of levels, wherein each of the plurality of levels corresponds to a sub-frequency range in a frequency range that corresponds to a type of biosignals received by the wearable biosignal sensor.

9. The wearable biosignal sensor of claim 8, wherein to filter the biosignals via the plurality of domain filters to identify abnormal biosignals further comprises to perform a spectral energy estimation of the biosignals transformed in the spectral domain.

10. The wearable biosignal sensor of claim 9, wherein to filter the biosignals via the plurality of domain filters to identify abnormal biosignals further comprises to determine whether the biosignals are abnormal based on the spectral energy estimation and a frequency domain threshold.

11. The wearable biosignal sensor of claim 9, wherein to perform the spectral energy estimation of the biosignals transformed in the spectral domain comprises to calculate an energy density of wavelet coefficients at each of the plurality of levels.

12. The wearable biosignal sensor of claim 11, wherein to perform the spectral energy estimation of the biosignals transformed in the spectral domain further comprises to calculate a total spectral energy density of the biosignals across each of the plurality of levels.

13. The wearable biosignal sensor of claim 12, wherein to perform the spectral energy estimation of the biosignals transformed in the spectral domain further comprises to calculate a relative spectral energy density as a function of the energy density of wavelet coefficients at the each of the plurality of levels and the total spectral energy density.

14. The wearable biosignal sensor of claim 1, wherein the wearable biosignal sensor is configured to capture data points at a rate of at least 100 Hertz.

15. The wearable biosignal sensor of claim 14, wherein the wearable biosignal sensor is configured to continuously capture and process biosignal data in real time.

16. A method for the filtering of abnormal biosignals, the method comprising:
  receiving, by a wearable biosignal sensor coupled to a user, biosignals of the user including a first biosignal;
  filtering, by the wearable biosignal sensor, the biosignals using a plurality of domain filters to identify abnormal biosignals, wherein the plurality of domain filters comprises a first stage domain classifier filter and a second stage domain classifier filter, wherein filtering the biosignals comprises:
    filtering, with the first stage domain classifier filter, the first biosignal to determine if the first biosignal is abnormal based on the first stage domain classifier filter;
    in response to a determination that the first biosignal is abnormal based on the first stage domain classifier filter, sending the first biosignal to the second stage domain classifier filter; and
    filtering, with the second stage domain classifier filter, the first biosignal to determine if the first biosignal is abnormal based on the second stage domain classifier filter; and
  in response to a determination that the first biosignal is abnormal based on the second stage domain classifier filter, transmitting, by the wearable biosignal sensor, the first biosignal to a computing device.

17. The method of claim 16, wherein filtering the biosignals using the second stage domain classifier filter comprises filtering the biosignals using a domain classifier filter in an orthonormal domain of the first stage domain classifier filter.

18. The method of claim 16, wherein filtering the biosignals using the plurality of domain filters to identify abnormal biosignals comprises (i) transforming the biosignals into a spectral domain via a filter bank that includes a plurality of levels, each of the plurality of levels corresponding to a sub-frequency range in a frequency range that corresponds to a type of biosignals being received by the wearable biosignal sensor, (ii) performing a spectral energy estimation of the biosignals transformed in the spectral domain, and (iii) determining whether the biosignals are abnormal based on the spectral energy estimation and a frequency domain threshold.

19. The method of claim 18, wherein performing the spectral energy estimation of the biosignals transformed in the spectral domain comprises (i) calculating an energy density of wavelet coefficients at each of the plurality of levels, (ii) calculating a total spectral energy density of the biosignals across each of the plurality of levels, and (iii) calculating a relative spectral energy density as a function of the energy density of wavelet coefficients at each of the plurality of levels and the total spectral energy density.

20. One or more non-transitory computer-readable storage media comprising a plurality of instructions stored thereon that in response to being executed cause a biosignal sensor to:
  receive, by a wearable biosignal sensor coupled to a user, biosignals of the user including a first biosignal;
  filter, by the wearable biosignal sensor, the biosignals using a plurality of domain filters to identify abnormal biosignals, wherein the plurality of domain filters comprises a first stage domain classifier filter and a second stage domain classifier filter, wherein to filter the biosignals comprises to:
    filter, with the first stage domain classifier filter, the first biosignal to determine if the first biosignal is abnormal based on the first stage domain classifier filter;
    in response to a determination that the first biosignal is abnormal based on the first stage domain classifier filter, send the first biosignal to the second stage domain classifier filter; and
    filter, with the second stage domain classifier filter, the first biosignal to determine if the first biosignal is abnormal based on the second stage domain classifier filter; and
  transmit, by the wearable biosignal sensor, the first biosignal to a computing device.

21. The one or more non-transitory computer-readable storage media of claim 20, wherein filtering the biosignals using the second stage domain classifier filter comprises filtering the biosignals using a domain classifier filter in an orthonormal domain of the first stage domain classifier filter.

22. The one or more non-transitory computer-readable storage media of claim 20, wherein filtering the biosignals using the plurality of domain filters to identify abnormal biosignals comprises transforming the biosignals into a spectral domain via a filter bank that includes a plurality of levels, each of the plurality of levels corresponding to a sub-frequency range in a frequency range that corresponds to a type of biosignals being received by the wearable biosignal sensor.

23. The one or more non-transitory computer-readable storage media of claim 22, wherein filtering the biosignals using the plurality of domain filters to identify abnormal biosignals further comprises performing a spectral energy estimation of the biosignals transformed in the spectral domain and determining whether the biosignals are abnormal based on the spectral energy estimation and a frequency domain threshold.

24. The one or more non-transitory computer-readable storage media of claim 23, wherein performing the spectral energy estimation of the biosignals transformed in the spectral domain comprises calculating an energy density of wavelet coefficients at each of the plurality of levels.

25. The one or more non-transitory computer-readable storage media of claim 24, wherein performing the spectral energy estimation of the biosignals transformed in the spectral domain further comprises calculating a total spectral energy density of the biosignals across each of the plurality of levels and calculating a relative spectral energy density as a function of the energy density of wavelet coefficients at the each of the plurality of levels and the total spectral energy density.

\* \* \* \* \*